(12) United States Patent
Erickson

(10) Patent No.: US 10,994,914 B2
(45) Date of Patent: May 4, 2021

(54) STORAGE PRODUCT AND METHOD

(71) Applicant: COOLSAN HYGIENE SOLUTIONS PTY LTD, Cremorne (AU)

(72) Inventor: Gary R. Erickson, Coonabarabran (AU)

(73) Assignee: Coolsan Hygiene Solutions PTY LTD, Cremorne (AU)

(*) Notice: Subject to any disclaimer, the term of this patent is extended or adjusted under 35 U.S.C. 154(b) by 36 days.

(21) Appl. No.: 15/330,564

(22) PCT Filed: Mar. 18, 2015

(86) PCT No.: PCT/AU2015/000153
§ 371 (c)(1),
(2) Date: Sep. 20, 2016

(87) PCT Pub. No.: WO2015/139075
PCT Pub. Date: Sep. 24, 2015

(65) Prior Publication Data
US 2017/0217661 A1     Aug. 3, 2017

(30) Foreign Application Priority Data
Mar. 18, 2014    (AU) ................................ 2014900941

(51) Int. Cl.
*B65D 81/26*     (2006.01)
*F24F 3/14*      (2006.01)
(Continued)

(52) U.S. Cl.
CPC ........... *B65D 81/264* (2013.01); *A01N 25/18* (2013.01); *A61L 2/20* (2013.01); *A61L 2/208* (2013.01);
(Continued)

(58) Field of Classification Search
CPC ......... B65D 81/264; A61L 9/12; A61L 2/208; A61L 2/20; A01N 25/18; A01N 59/00; A01N 59/14; F24F 3/1411
See application file for complete search history.

(56) References Cited

U.S. PATENT DOCUMENTS

| 4,863,688 A | 9/1989 | Schmidt et al. |
| 5,792,422 A | 8/1998 | Lin et al. |

(Continued)

FOREIGN PATENT DOCUMENTS

| EP | 0261422 | 3/1988 |
| EP | 2179748 | 4/2010 |

(Continued)

OTHER PUBLICATIONS

Database WPI Week 200727, Thomson Scientific, London, GB; AN 2007-277930, XP002773869.
(Continued)

*Primary Examiner* — Regina M Yoo
(74) *Attorney, Agent, or Firm* — Hoffmann & Baron, LLP

(57) ABSTRACT

A device and method for the provision of antimicrobial activity and/or moisture protection for goods and other items prone to damage caused by microbes and/or water, such as, for example, foodstuffs and other putrescible items, pharmaceuticals and other medical/veterinary products, paper and paper/fibre-board products, timber and wood products, electrical/electronic devices, clothes and fabrics, is disclosed. The device and method is particularly suitable for use with such goods and other items when contained within storage spaces (eg a package, refrigerator, wardrobe or shipping container). The device comprises a vapour-permeable container housing a moisture-removing material and an antimicrobial vapour-generating material in an arrangement such that water added to the device or absorption and/or adsorption of water vapour by the moisture-removing mate- (Continued)

rial causes the antimicrobial vapour-generating material to generate an antimicrobial vapour. A device and method for disinfecting items such as food containers and food preparation implements, is also disclosed.

5 Claims, 2 Drawing Sheets

(51) Int. Cl.
  *A01N 25/18* (2006.01)
  *A61L 2/20* (2006.01)
  *A61L 9/12* (2006.01)
(52) U.S. Cl.
  CPC ............... *A61L 9/12* (2013.01); *F24F 3/1411* (2013.01); *A61L 2202/11* (2013.01)

(56) References Cited

U.S. PATENT DOCUMENTS

| | | |
|---|---|---|
| 6,592,919 B1 | 7/2003 | Matthews et al. |
| 7,229,599 B2 | 6/2007 | Horacek et al. |
| 8,361,409 B2* | 1/2013 | Rico ..................... A01N 37/16 206/205 |
| 8,920,716 B2 | 12/2014 | Erickson |
| 2003/0124026 A1 | 7/2003 | Williams et al. |
| 2005/0053517 A1 | 3/2005 | Finan et al. |
| 2006/0039841 A1* | 2/2006 | Rico ..................... A01N 37/16 422/305 |
| 2006/0065200 A1* | 3/2006 | Jenkins ................. A23K 50/70 119/51.01 |
| 2006/0160711 A1* | 7/2006 | Frank ..................... C11D 3/373 510/101 |
| 2006/0280665 A1 | 12/2006 | Rees et al. |
| 2009/0142235 A1 | 6/2009 | Rico et al. |
| 2009/0148342 A1* | 6/2009 | Bromberg ............. A01N 59/00 422/37 |
| 2011/0253562 A1 | 10/2011 | Machado |
| 2013/0059765 A1* | 3/2013 | Leininger ............ C11D 3/3942 510/376 |
| 2013/0302480 A1 | 11/2013 | Gandhi et al. |
| 2015/0284249 A1* | 10/2015 | Fujita ..................... A01N 25/18 422/239 |

FOREIGN PATENT DOCUMENTS

| | | |
|---|---|---|
| JP | 11239608 | 9/1999 |
| JP | 2002-212013 A | 7/2002 |
| JP | 2003-275633 A | 9/2003 |
| JP | 2007-176931 A | 7/2007 |
| KR | 20090066651 | 6/2009 |
| WO | 2001006876 | 2/2001 |
| WO | 2007/070922 A1 | 6/2007 |
| WO | 2011023560 | 3/2011 |
| WO | 2011072326 | 6/2011 |
| WO | 2012/075547 A1 | 6/2012 |
| WO | 2012156685 | 11/2012 |

OTHER PUBLICATIONS

Database WPI Week 201358, Thomson Scientific, London, GB; AN 2013-M31248, XP002773870.

Extended European Search Report, EP 15765579, dated Sep. 29, 2017.

Japanese Office Action for Japanese Application No. 2017-500099, dated Apr. 2, 2019 (14 pages, with translation).

* cited by examiner

STORAGE PRODUCT AND METHOD

TECHNICAL FIELD

The present invention relates to the storage and/or packaging of goods and other items prone to damage caused by microbes and/or water, such as, for example, foodstuffs and other putrescible items, pharmaceuticals and other medical/veterinary products, paper and paper-/fibre-board products, timber and wood products, electrical/electronic devices, clothes and fabrics. More particularly, the present invention relates to a device and method for the provision of antimicrobial activity and/or moisture protection for goods and other items when contained within storage spaces (eg a package, refrigerator, wardrobe or shipping container). The present invention also relates to a device and method for disinfecting an item such as food containers and food preparation implements.

INCORPORATION BY REFERENCE

The following patent is referred to in the following description:

Australian Patent No 2006202977 titled "In-situ continuous enclosed or semi-enclosed space sanitation and deodorization" filed on 12 Jul. 2006 claiming priority from Australian Provisional Patent Application No 2005907187. The content of this patent is hereby incorporated by reference in its entirety.

BACKGROUND

Microbial contamination of goods (especially during storage) or other items (which may either be in regular use or placed in storage for a period of time), can have significant adverse impacts on those goods or items (or the users or consumers of those goods or items), particularly in cases where the goods are foodstuffs or the items are food containers or food preparation implements. Approaches to preventing microbial activity can involve the reduction of moisture, disinfection of the goods or items, or the prolonged or continuous application of an antimicrobial agent while the goods or items are in storage.

In particular, in the context of stored goods and other items, contamination by microbes (eg bacteria, moulds and fungi) may lead to damage in the form of stains, discolouration, rot and/or microbial spoilage. In addition, the presence of moisture (ie water vapour and/or liquid) can also cause (or exacerbate) goods damage such as the formation of water marks, discolouration, corrosion (eg rust), deformation (eg collapse) and/or reduced structural integrity (particularly of paper-/fibre-board products or packaging). Such damage can often be accompanied by malodours (eg mustiness in wardrobes). Moreover, microbial and/or water damage may also lead to insect infestation and associated damage.

In the context of shipping containers, the loss and cost associated with microbial and/or water damage to shipped goods can be very considerable. However, even though a tightly closed shipping container provides excellent protection of the goods from the effects of rain, snow, salt spray, dust, excessive heat and ultraviolet light, providing adequate protection against microbial and/or water damage can be a great challenge as shipping containers can be exposed to considerable climatic variation (eg variable temperature and humidity), particularly during longer periods of transportation, which may lead to condensation on the goods (ie "cargo sweat") or internal surfaces of the container (ie "container rain"). In turn, this condensation may lead to microbial and/or water damage of the goods as described above.

To overcome the problem of microbial and/or water damage of goods in shipping containers and other storage situations, inexpensive solutions, mostly based upon the desiccant ability of certain materials, have been employed. For example, for shipping containers, a common approach has been to include a desiccant material such as silica gel in the shipping container itself and/or inside individual packages within the shipping container. This approach does, however, achieve only variable results and, notably, does not have any direct action on the inhibition of damage-causing microbes. That is, desiccant materials only prevent microbial damage of goods by reducing the amount of water present to a level whereby microbial growth may be inhibited.

Previously, it has been disclosed that an approach to preventing microbial damage of goods and other items contained within a confined storage space, can involve the creation of an equilibrium concentration of a suitable chemical disinfectant vapour such as hydrogen peroxide vapour (see Australian Patent No 2006202977). This approach offers the advantage over the use of a dessicant material, such as silica gel, by achieving microbial decontamination of the storage space; that is, with continuous application of the vapour, microbial growth within the storage space may be reduced. However, while excellent results have been achieved, particularly in the context of domestic refrigerators and wardrobes, some limitations to the application and/or effectiveness of this approach are provided by the need to employ liquid chemical solutions (eg hydrogen peroxide solutions) which may have a relatively short shelf-life and require precautions to be taken to prevent both the user from coming into contact with the solutions and the solutions from contacting the stored goods or other items. It has also been noted that the relative humidity within the storage space may have a considerable impact on the efficacy of the approach. In addition, the approach disclosed in Australian Patent No 2006202977 does not inhibit or remove the presence of water moisture within the storage space.

SUMMARY

The present invention is directed to the provision of a novel device and method to prevent microbial and/or water damage of goods and other items contained within a storage space such as a package, refrigerator, wardrobe, shipping container, cool room etc. The invention may overcome and/or ameliorate one or more of the problems or disadvantages of the previous approaches described above.

In a first aspect, the present invention provides a device comprising a vapour-permeable container which houses:

(i) a moisture-removing material, and
(ii) an antimicrobial vapour-generating material;

wherein said moisture-removing material and antimicrobial vapour-generating material are provided in an arrangement such that water added to the device (eg by direct addition) or absorption and/or adsorption of water vapour by the moisture-removing material causes the antimicrobial vapour-generating material to generate an antimicrobial vapour.

In a second aspect, the present invention provides a method to prevent microbial and/or water damage of goods and other items contained within a storage space, wherein said method comprises:

(1) providing a device comprising a container which houses
   (i) a moisture-removing material, and
   (ii) an antimicrobial vapour-generating material,
in an arrangement such that water added to the device (eg by direct addition) or absorption and/or adsorption of water vapour by the moisture-removing material causes the antimicrobial vapour-generating material to generate an antimicrobial vapour; and
(2) introducing said device into the storage space.

In a third aspect, the present invention provides a method to remove ethylene and/or odoriferous compounds present in a storage space, wherein said method comprises:
(1) providing a device comprising a container which houses
   (i) a moisture-removing material, and
   (ii) an antimicrobial vapour-generating material,
in an arrangement such that water added to the device (eg by direct addition) or absorption and/or adsorption of water vapour by the moisture-removing material causes the antimicrobial vapour-generating material to generate an antimicrobial vapour which reacts with ethylene and/or odoriferous compounds; and
(2) introducing said device into the storage space.

The present invention is also directed to the provision of a novel device and method for disinfecting items such as baby bottles and food containers.

Thus, in a fourth aspect, the present invention provides a method of disinfecting an item, wherein said method comprises:
(1) providing a device comprising
   (i) a moisture-removing material, and
   (ii) an antimicrobial vapour-generating material,
in an arrangement such that water added to the device (eg by direct addition) or absorption and/or adsorption of water vapour by the moisture-removing material causes the antimicrobial vapour-generating material to generate an antimicrobial vapour; and
(2) introducing said device into a disinfection chamber with the said item.

In a fifth aspect, the present invention provides a device in the form of a tablet or pellet or the like comprising a formulation of a moisture-removing material and an antimicrobial vapour-generating material, optionally enveloped within a vapour-permeable or water-soluble layer, coating or film, wherein said moisture-removing material and antimicrobial vapour-generating material are provided in an arrangement such that absorption and/or adsorption of water vapour by the moisture-removing material causes the antimicrobial vapour-generating material to generate an antimicrobial vapour.

DETAILED DESCRIPTION

Figure 1A:
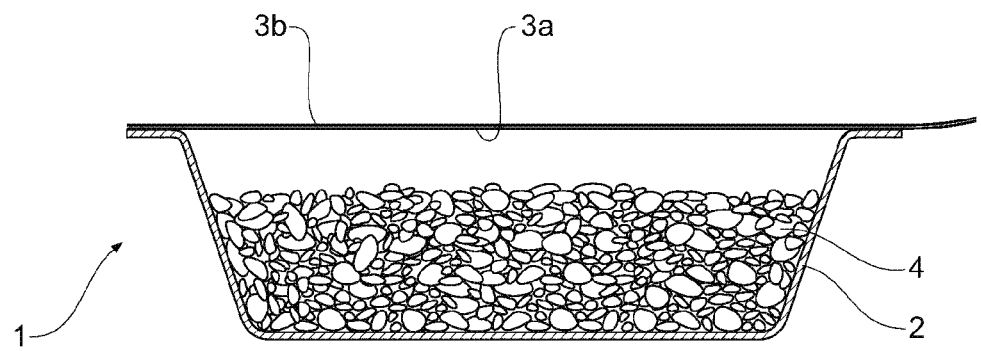
FIG. 1 shows various embodiments of the device of the invention: (A) and (B) provide schematic, cross-sectional views of two devices comprising a bowl-like container; and (C) provides a schematic, cross-sectional side view of a device comprising a sachet.

The present invention provides, in a first aspect, a device comprising a vapour-permeable container which houses:
   (iii) a moisture-removing material, and
   (iv) an antimicrobial vapour-generating material;
wherein said moisture-removing material and antimicrobial vapour-generating material are provided in an arrangement such that water added to the device (eg by direct addition) or absorption and/or adsorption of water vapour by the moisture-removing material, causes the antimicrobial vapour-generating material to generate an antimicrobial vapour.

The device of the invention is intended for use in the prevention of microbial and/or water damage of stored goods or other items contained within a storage space such as a confined storage space (eg a package, refrigerator, cool room, wardrobe, cupboard, pantry or shipping container (including refrigerated (a "reefer") and/or controlled atmosphere (CA) shipping containers)). In such uses, moisture within the storage space may be removed by the absorption and/or adsorption of water vapour that has permeated into the container by said moisture-removing material. As such, it is preferable that the moisture-removing material and antimicrobial vapour-generating material are provided in an arrangement such that the absorption and/or adsorption of water vapour by the moisture-removing material can cause the antimicrobial vapour-generating material to generate an antimicrobial vapour. The antimicrobial vapour can then permeate from the container into the storage space and exert an antimicrobial effect (ie inhibit microbial growth and/or kill microbes) on microbes (eg bacteria, moulds and fungi) present in the storage space. Alternatively, the device may be activated (ie to cause the antimicrobial vapour-generating material to generate an antimicrobial vapour) by the addition of water to the device (eg by direct addition by briefly placing the device under a running tap or by the use of a pipette or dropper).

The moisture-removing material may be selected from a wide variety of suitable materials including dessicant materials well known to those skilled in the art such as silica gel (silicon dioxide; $SiO_2$) and activated charcoal, and other hygroscopic substances including calcium chloride ($CaCl_2$), calcium sulphate ($CaSO_4$), porous glass, and various clay and zeolite materials. Such materials, including the examples of calcium chloride and calcium sulphate, are preferably provided in a dry form (ie without any free moisture). Also, such materials are preferably provided in a particulate (eg fine powder) or granular form providing a high specific surface area (SSA) of, for example, >100 $m^2$ $g^{-1}$, or more preferably >200 $m^2$ $g^{-1}$, and may preferably be characterised by a loose bulk density of, for example, >0.2 $g/cm^3$, more preferably >0.28 $g/cm^3$.

In some embodiments of the invention, the moisture-removing material may be provided in combination with a solid substrate providing a high specific surface area (SSA) of, for example, >100 $m^2$ $g^{-1}$, more preferably >200 $m^2$ $g^{-1}$. Suitable examples of such a substrate include precipitated silica (eg Tokusil 195G; Redox Pty Ltd, Minto, NSW, Australia), polymeric films or polymeric fibres (optionally provided as a woven or non-woven mesh or fabric such as 3M absorbent cloth (Scotch-Brite® kitchen cloth); 3M Corporation, St Paul, Minn., United States of America), and other materials such as natural vermiculite and molecular sieves. In some particular embodiments, the substrate may be silica gel, in which case the dessicant ability of the substrate may complement the moisture-removing capacity of the moisture-removing material. The moisture-removing material and the substrate may be provided as a composition comprising each of said moisture-removing material and substrate in, for example, a simple admixture or, alternatively, as a coating (preferably, a partial coating) of one on the other. One particular example of this latter arrangement consists of a substrate comprising a polymeric film or polymeric fibres (optionally provided as a woven or non-woven mesh or fabric) coated or partially coated with the moisture-removing material. Another particular example consists of a particulate or granular substrate (eg silica gel) wherein the particles/granules are coated or partially coated with the moisture-removing material.

Coatings on a substrate may be readily prepared, for example, by applying a solution of the moisture-removing material to the solid substrate, and thereafter removing the solvent (eg by drying) to produce a dry composition. The solution of the moisture-removing material may optionally be applied to the solid substrate with a surfactant, preferably a surfactant that is resistant to degradation by hydrogen peroxide and/or other reactive oxygen species (ROS). Examples of such surfactants include sodium polyacrylate and fluorinated surfactants, etc.

Preferably, in a composition comprising the moisture-removing material and said substrate, the amount of the moisture-removing material is in the range of 5-70% by weight of the dry composition (wt %) and the amount of the substrate is in the range of 20-85% wt %. More preferably, the amount of the moisture-removing material is in the range of 25-60 wt % and the amount of the substrate is in the range of 40-75% wt %.

The antimicrobial vapour-generating material may be selected from any material which, upon exposure to or contact with moisture (ie as a consequence of the absorption and/or adsorption of water vapour by the moisture-removing material), is capable of generating an antimicrobial vapour such as a vapour comprising hydrogen peroxide and/or other reactive oxygen species (ROS) including oxygen radicals (eg the peroxide radical (HO—) and the superoxide anion ($O_2^-$)). For the purposes of the present invention, a vapour is regarded as being "antimicrobial" if, exposure of a test microorganism (namely, *Pseudomonas aeruginosa* (Schroeter) Migula, ATCC 9027; American Type Culture Collection, Manassas, Va., United States of America) to an atmosphere comprising at least 0.05 ppm of the vapour in air, results in a reduction in the viable population (cfu; colony forming units) of the microorganism.

In some embodiments of the invention, the antimicrobial vapour-generating material is preferably selected from materials which generate hydrogen peroxide vapour upon exposure to or contact with moisture. Preferably, such materials are provided in a dry form. Suitable examples include sodium percarbonate ($Na_2CO_3.1.5H_2O_2$), hydrated sodium perborate ($NaBO_3._nH_2O$), and various organic or inorganic peroxy salts (eg urea hydrogen peroxide ($H_2NCONH_2.H_2O_2$), benzyl peroxide ($[C_6H_5C(O)]_2O_3$), lithium peroxide ($Li_2O_2$), and sodium peroxide ($Na_2O_2$)), and combinations thereof. However, preferably, the antimicrobial vapour-generating material is sodium percarbonate. Upon exposure to or contact with moisture, sodium percarbonate dissolves and releases hydrogen peroxide and sodium carbonate:

$$2\ Na_2CO_3.1.5H_2O_2 \rightarrow 2\ Na_2CO_3 + 3\ H_2O_2$$

The moisture-removing material and antimicrobial vapour-generating material are provided in the container in an arrangement such that, preferably, absorption and/or adsorption of water vapour by the moisture-removing material causes the antimicrobial vapour-generating material to generate an antimicrobial vapour. In some embodiments of the invention, such an arrangement consists in the provision of a composition comprising each of said moisture-removing material and antimicrobial vapour-generating material in, for example, a simple admixture or layered arrangement (eg a layer of the antimicrobial vapour-generating material on top of a layer of the moisture-removing material) or, alternatively, as a coating (preferably, a partial coating) of one on the other. In all such arrangements, through the absorption and/or adsorption of water vapour by the moisture-removing material, the intimate association of the moisture-removing material and antimicrobial vapour-generating material ensures that the antimicrobial vapour-generating material is exposed to or contacts water moisture consequently causing the generation of antimicrobial vapour.

Preferably, the moisture-removing material and antimicrobial vapour-generating material are provided as a composition wherein the antimicrobial vapour-generating material is a coating (preferably, a partial coating) on the surface of particles/granules of the moisture-removing material (eg sodium percarbonate on silica gel). Such a coating may be readily prepared, for example, by applying a solution of the antimicrobial vapour-generating material to the moisture-removing material, and thereafter removing the solvent (eg by drying) to produce a dry composition. By "drawing" water vapour through the coating of antimicrobial vapour-generating material, the moisture-removing material ensures that the antimicrobial vapour-generating material is exposed to or contacts water moisture which consequently causes the generation of antimicrobial vapour.

Preferably, in a composition comprising the moisture-removing material and antimicrobial vapour-generating material, the amount of the moisture-removing material is in the range of 20-85% by weight of the dry composition (wt %) and the amount of the antimicrobial vapour-generating material is in the range of 5-50 wt %. More preferably, the amount of the moisture-removing material is in the range of 50-75 wt % and the amount of the antimicrobial vapour-generating material is in the range of 10-40 wt %.

Where the device of the invention employs a substrate, the moisture-removing material, antimicrobial vapour-generating material and the substrate may be provided as a composition in the form of, for example, a simple admixture or, alternatively, in an arrangement wherein one or both of said moisture-removing material and antimicrobial vapour-generating material is/are provided as a coating (preferably, a partial coating) of the substrate. One particular example of this latter arrangement consists of a substrate comprising a polymeric film or polymeric fibres (optionally provided as a woven or non-woven mesh or fabric) coated or partially coated with the moisture-removing material and antimicrobial vapour-generating material. Another particular example consists of a particulate or granular substrate wherein the particles/granules are coated or partially coated with the moisture-removing material and antimicrobial vapour-generating material, such as precipitated silica coated/partially coated in calcium chloride and sodium percarbonate. Such a coating may be readily prepared, for example, by applying a solution(s) of the moisture-removing material and antimicrobial vapour-generating material to the solid substrate, and thereafter removing the solvent to produce a dry composition. The solution of the moisture-removing material may optionally be applied to the solid substrate with a suitable surfactant (eg sodium polyacrylate, a fluorinated surfactant, etc).

Preferably, in a composition comprising the moisture-removing material, antimicrobial vapour-generating material and a substrate, the amount of the moisture-removing material is in the range of 20-50% by weight of the dry composition (wt %), the amount of the antimicrobial vapour-generating material is in the range of 10-30 wt % and the amount of the substrate is in the range of 35-90% wt %. More preferably, the amount of the moisture-removing material is in the range of 20-40 wt %, the amount of the antimicrobial vapour-generating material is in the range of 10-20 wt %, and the amount of the substrate is in the range of 45-65% wt %.

In embodiments of the invention where a surfactant is included, the amount of the surfactant will typically be present in the range of 0.01-2.0 wt %, more preferably 0.05-1.0 wt %.

Preferably, the moisture-removing material, antimicrobial vapour-generating material and any substrate is substantially free of ions or compounds that may inhibit the formation of the antimicrobial vapour. For example, preferably, the moisture-removing material, antimicrobial vapour-generating material and any substrate is substantially free of ferrous or other transition metal ions (ie less than 2 wt % of any of all of the moisture-removing material, antimicrobial vapour-generating material and substrate) that may inhibit the generation of hydrogen peroxide vapour.

The device of the invention may be of many different forms. For example, the device may comprise a container that is of bowl-like appearance or consists of a bucket or box. However, more preferably, the device comprises a sachet-type container. Preferably, all such containers shall be vapour-permeable such that water vapour from a storage space may permeate into the container and antimicrobial vapour (eg hydrogen peroxide) generated from the antimicrobial vapour-generating material may permeate into the storage space. Preferably, the container is impermeable to water liquid and/or droplets. Various embodiments of the device of the invention are shown in FIG. 1.

Particularly, FIG. 1A shows a device comprising a bowl-like container (1) composed of rigid moisture- and vapour-impermeable polymer (eg a thermoplastic polymer such as polyethylene terephthalate (PET), polyethylene (PE), high or low density polyethylene (HDPE, LDPE), polytetrafluoroethylene (PTFE)) walls (2) provided with a 2-ply film closure (3) comprising an inner, vapour-permeable film (3a) (that is also impermeable to water liquid and/or droplets) composed of a non-woven HDPE fibre such as Tyvek® (Dupont Corporation, Wilmington, Del. United States of America) or other porous material such as expanded PTFE, and an outer, moisture- and vapour-impermeable film (3b) (eg composed of vinyl, HDPE or aluminium foil) that is removably adhered to the inner film (3a) such that, just prior to use, the outer film (3b) may be removed (eg peeled) from the inner film (3a) thereby enabling water vapour and the antimicrobial vapour to permeate across the inner film (3a). In an alternative to this embodiment, the bowl-like container of the device comprises a film closure comprising a vapour-permeable film only, which can be stored prior to use in a sealed moisture- and vapour-impermeable bag. In FIG. 1A, the container houses precipitated silica substrate coated with calcium chloride, sodium percarbonate and sodium polyacrylate (4).

Figure 1B:
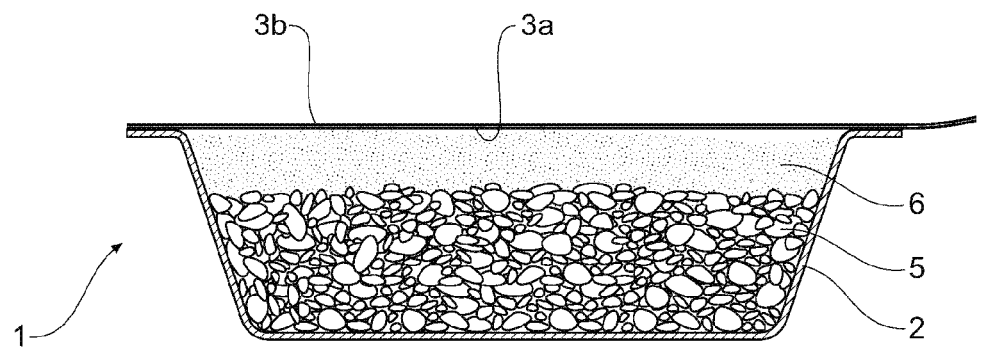

In FIG. 1B, another alternative to the embodiment shown in FIG. 1A is shown. In this embodiment, the device comprises a container (1) housing a water-removing material (5) provided in a lower layer underneath an upper layer of an antimicrobial vapour-generating material (6) in a dry powdered form. The container (1) is packed tightly with minimal, if any, headspace such that disturbance of the layers is minimised, and the arrangement is such that water vapour that permeates across the vapour-permeable film (3a) and into the container (1) is "drawn" through the antimicrobial vapour-generating material to the water-removing material. In FIG. 1B, the container houses a lower layer of silica gel (5) and an upper layer of sodium percarbonate (6).

Figure 1C:
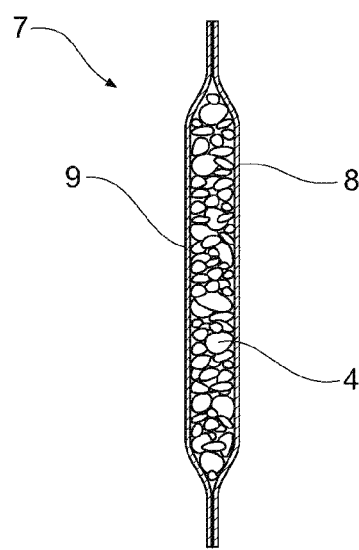

In FIG. 1C, a device is shown comprising a preferred sachet-type container (7) comprising vapour-permeable walls (8, 9) composed of, for example, a non-woven HDPE fibre membrane (that is also impermeable to water liquid and/or droplets) housing precipitated silica substrate coated with calcium chloride, sodium percarbonate and sodium polyacrylate (4). The sachet container (7) is packed tightly with minimal, if any, headspace. Prior to use, the device can be stored in a sealed moisture- and vapour-impermeable bag. The device may be provided with an adhesive strip to removably adhere the device to a convenient position within a storage space (eg a wall or door of a refrigerator).

In a second aspect, the present invention provides a method to prevent microbial and/or water damage of goods and other items contained within a storage space, wherein said method comprises:

(1) providing a device comprising a container which houses
    (i) a moisture-removing material, and
    (ii) an antimicrobial vapour-generating material,
in an arrangement such that water added to the device (eg by direct addition) or absorption and/or adsorption of water vapour by the moisture-removing material causes the antimicrobial vapour-generating material to generate an antimicrobial vapour; and (2) introducing said device into the storage space.

The method of the invention is suitable for preventing microbial and/or water damage of goods and other items contained within a storage space such as a confined storage space such as a package, refrigerator, cool room, wardrobe, cupboard, pantry or shipping container. The goods and other items may, therefore, be selected from, for example, foodstuffs and other putrescible items, pharmaceuticals and other medical/veterinary products, paper and paper-/fibre-board products, timber and wood products, electrical/electronic devices, clothes and fabrics.

In addition to the antimicrobial effect, the generated antimicrobial vapour may also beneficially react with and thereby remove ethylene (which may, for example, hasten ripening or spoilage of fresh fruit and vegetables) and odoriferous compounds present in the storage space.

Thus, in a third aspect, the present invention provides a method to remove ethylene and/or odoriferous compounds present in a storage space, wherein said method comprises:

(1) providing a device comprising a container which houses
    (i) a moisture-removing material, and
    (ii) an antimicrobial vapour-generating material,
in an arrangement such that water added to the device (eg by direct addition) or absorption and/or adsorption of water vapour by the moisture-removing material causes the antimicrobial vapour-generating material to generate an antimicrobial vapour which reacts with ethylene and/or odoriferous compounds; and (2) introducing said device into the storage space.

The device employed in the method of the second or third aspect may be as described above in connection to the first aspect of the present invention.

The device employed in the method of the second or third aspect need not, however, comprise a vapour-permeable container. That is, the device may be of a construction that is vapour-impermeable, but is simply punctured or otherwise opened (eg by removal of a seal to an opening in the container) by the user at the time of introducing the device into the storage space (such as a confined storage space), thereby enabling water vapour from the storage space to enter the container and antimicrobial vapour to exit out of the container into the storage space. Alternatively, the device may be activated (ie to cause the antimicrobial vapour-generating material to generate an antimicrobial vapour) by the addition of water to the device (eg by direct addition through a puncture or opening by briefly placing the device under a running tap or by the use of a pipette or dropper).

When employed in the method of the first aspect, the device is intended to generate an atmosphere within the storage space comprising a concentration of the antimicrobial vapour that, in some embodiments, is non-hazardous to users but still effective in treating the storage space (ie the concentration of the antimicrobial vapour is very low but still sufficient to exert an antimicrobial effect). As will be understood by those skilled in the art, such a concentration may be temperature-dependent (ie the concentration will vary with the temperature within the storage space), but will preferably be ≤1 ppm. For hydrogen peroxide vapour, the recommended safe limit (TLV-TWA 8 hours) in the workplace is 1.4 mg/kg air (1 ppm) (Hydrogen Peroxide-US Centers for Disease Control and Prevention; http://www.cdc.gov/niosh/idlh/772841.html) and, accordingly, in embodiments of the present invention wherein hydrogen peroxide vapour is generated from the antimicrobial vapour-generating material, the method is preferably conducted such that the maximum concentration of hydrogen peroxide in the storage space is ≤1 ppm. However, in other embodiments, the device may be intended to generate an atmosphere within the storage space (such as a confined storage space) comprising a concentration of the antimicrobial vapour that is ≤10 ppm or, more preferably, ≤1000 ppm.

The device may be introduced into the storage space by simply placing the device in a convenient position. To this end, for certain forms of the device (eg a device comprising a sachet-type container), the device may optionally be provided with an adhesive strip to enable the user to removably adhere the device to a convenient position within the storage space.

The device of the present invention may also be adapted for use in the rapid disinfection of various items such as food containers and food preparation implements (eg knives), and medical devices and instruments. For example, a sachet-type device according to the present invention (ie as described above) may be introduced into a suitable chamber for disinfection along with an item or items to be disinfected. By, for example, directly adding a small amount of water into device within the chamber may then cause the antimicrobial vapour-generating material to generate an antimicrobial vapour to disinfect the said item(s).

Thus, in a fourth aspect, the present invention provides a method of disinfecting an item, wherein said method comprises:
(1) providing a device comprising
  (i) a moisture-removing material, and
  (ii) an antimicrobial vapour-generating material, in an arrangement such that water added to the device (eg by direct addition) or absorption and/or adsorption of water vapour by the moisture-removing material causes the antimicrobial vapour-generating material to generate an antimicrobial vapour; and
(2) introducing said device into a disinfection chamber with the said item.

The device employed in the method of the fourth aspect may be as described above in connection to the first aspect of the present invention. That is, the device may comprise a container housing the moisture-removing material and antimicrobial vapour-generating material as described above. Alternatively, the device may comprise a tablet or pellet or the like comprising the moisture-removing material and antimicrobial vapour-generating material. Such a tablet or pellet may be enveloped within a vapour-permeable layer, coating or film (eg composed of a non-woven HDPE fibre or other porous material such as expanded PTFE) or a water-soluble external layer, coating or film (eg composed of, for example, gelatin, cellulose or other material well known to those skilled in the art). Additionally or alternatively, the tablet or pellet may be formed by simply compressing the formulation (optionally in the presence of a suitable binding agent such as povidone, xanthan gum and certain acrylic resins (eg Carbopol® polymers; The Lubrizol Corporation, Wickliffe, Ohio, United States of America) with a standard tablet press. The formulation may also comprise, for example, a disintegrant (eg cross-linked polyvinylpyrrolidone and other disintegrant excipients well known to those skilled in the art) to facilitate the tablet or pellet breaking apart upon exposure to water or water vapour.

Thus, in a fifth aspect, the present invention provides a device in the form of a tablet or pellet or the like comprising a formulation of a moisture-removing material and an antimicrobial vapour-generating material, optionally enveloped within a vapour-permeable or water-soluble layer, coating or film, wherein said moisture-removing material and antimicrobial vapour-generating material are provided in an arrangement such that absorption and/or adsorption of water vapour by the moisture-removing material causes the antimicrobial vapour-generating material to generate an antimicrobial vapour.

In use, the device of the fifth aspect is placed into a disinfection chamber with the said item(s) to be disinfected. The chamber may be of many different forms, such as a tube, bucket or tub. However, in all cases, the chamber will, preferably, be reversibly sealable (ie such that during disinfection, the chamber is sealed). Before sealing the chamber, it may be desirable or necessary to introduce a small amount of water to commence the generation of the antimicrobial vapour from the antimicrobial vapour-generating material; for example, the water may be required in order to produce water vapour that may permeate across a vapour-permeable layer, coating or film or to dissolve a water-soluble layer, coating or film enveloping the formulation. Further, to enhance the disinfection stage, it may be preferable to heat the chamber (eg to a temperature within the range of about 50° C. to about 80° C.) and/or adapt the formulation so as to achieve a relatively rapid generation of antimicrobial vapour (eg the formulation may comprise a relatively high amount of the antimicrobial vapour-generating material, compared to the amount of the moisture-absorbing material and solid substrate, if any). Preferably, the ratio of the amount of the antimicrobial vapour-generating material to moisture-absorbing material would be about 1:2, more preferably about 1:1.

The invention is hereinafter described with reference to the following, non-limiting example(s).

EXAMPLES

Example 1

Preparation of Device for Domestic Applications

Formulation

A formulation comprising a mixture of 55.0 wt % precipitated silica substrate (Tokusil 195G) with an SSA of 206 $m^2$ $g^{-1}$), 30.0 wt % of a moisture-removing material (namely, calcium chloride powder; CACHL05600, Redox Pty Ltd), 14.9% sodium percarbonate powder and 0.1% sodium polyacrylate powder is formed by simply combining the components in a suitable vessel. The resultant formulation comprises:

| | |
|---|---|
| Precipitated silica | 55.0 wt %, |
| Calcium chloride | 30.0 wt %, |
| Sodium percarbonate | 14.9 wt %, and |
| Sodium polyacrylate | 0.1 wt %. |

The formulation is then placed (in amounts of about 20 g) into 11 cm×10 cm sachets composed of a membrane of Tyvek® (which is vapour-permeable, but impermeable to moisture (ie impermeable to water liquid and/or droplets)). The sealed sachets are then packaged in a moisture- and vapour-impermeable bag composed of HDPE, until use.

Use

In use, the sachet is removed from the bag and placed into the desired confined storage space. For use in a typical family-sized, 500 L (0.5 $m^3$) domestic refrigerator, one sachet should be sufficient to provide protection against microbial damage to stored items such as foodstuffs and other putrescible foods (eg fresh fruit, vegetables, dairy products, seafood, poultry, meats and deli produce) for up to 3-4 weeks under normal use and conditions. It is estimated that the sachet generates an atmosphere within a 0.5 $m^3$ domestic refrigerator comprising a maximum concentration of hydrogen peroxide vapour of <0.5 ppm. In addition to the antimicrobial effect, the hydrogen peroxide vapour may also beneficially react with and thereby remove ethylene (which may, for example, hasten ripening or spoilage of fresh fruit and vegetables) and odoriferous compounds present in the refrigerator. The sachet may optionally be provided with an adhesive strip to enable the user to removably adhere the sachet to a convenient position on a wall or door of the refrigerator.

Discussion

The amount of the calcium chloride present in the sachet determines the maximum volume of water which can be removed from a confined storage space. In the amount employed in the exemplified sachet, it is anticipated that up to about 15 mL of water may be removed from the closed interior of a refrigerator. Although not wishing to be bound by theory, it is believed that as water is removed, a solution of calcium chloride is formed which spreads across the surface of the precipitated silica substrate (assisted by the sodium polyacrylate surfactant) simultaneously dissolving the sodium percarbonate and thereby producing a solution of hydrogen peroxide (from which a vapour of molecular hydrogen peroxide or radicals thereof may be generated to egress from the sachet and become available to achieve an antimicrobial effect within the closed interior of the refrigerator). As such, the ratio of the amount of calcium chloride to the amount of sodium percarbonate (in this case, about 2:1) determines the maximum volume of water that is extracted and the concentration of hydrogen peroxide in solution across the precipitated silica substrate (ie the greater the ratio, the higher the liquid volume achieved, the further the spread of the liquid over the precipitated silica substrate and the lower the final concentration of hydrogen peroxide in the liquid). Desirably, the sachet includes an amount of calcium chloride which extracts a maximum volume of water that may be fully contained by the surface of the precipitated silica substrate, so that the formation of water droplets or a small volume of liquid water within the sachet is prevented. The amount of 6 g of calcium chloride in the exemplified sachet achieves this outcome.

Example 2

Preparation of Device for Use in Shipping Containers

Formulation

A formulation comprising a precipitated silica substrate ((Tokusil 195G with an SSA of 206 $m^2$ $g^{-1}$) and calcium chloride can be prepared by first forming a solution of calcium chloride in ethanol (10% concentration), optionally using a surfactant such as a fluorinated surfactant, and then absorbing the calcium chloride solution onto the precipitated silica. The ethanol is then evaporated away at 110° C. and, once the precipitated silica substrate becomes dry, a homogeneous mixture (20 g/L) of sodium percarbonate solution and sodium polyacrylate (0.1 g/L) is then poured over the top to form a formulation that is substantially equivalent to that described in Example 1. The formulation is then allowed to dry under dry atmosphere conditions, before being placed (in amounts of about 145 g) into 140 cm×210 cm sachets composed of Tyvek® (which is vapour-permeable, but impermeable to moisture). The sealed sachets are then packaged in a moisture- and vapour-impermeable HDPE bag until use.

Use

For use in a standard sized shipping container having an internal volume of 25 $m^3$, the sachet is removed from the bag and placed inside of the container. Typically, the sachet will be provided with an adhesive strip to enable the user to conveniently and removably adhere the sachet to a convenient position on a wall or door of the container. Depending upon the nature of the goods (particularly the moisture content of the goods) and any packaging, one to five sachets may be placed in a container to prevent microbial and/or water damage to the goods for up to 3-4 weeks under normal shipping conditions.

Example 3

Preparation of Device for Rapid Disinfection

Formulation

A formulation was prepared as described in Example 1 and placed (in amounts of about 20 g) into 10 cm×15 cm sachets composed of a membrane of Tyvek®. The sealed sachets were then packaged in a moisture- and vapour-impermeable HDPE bag until use.

Use

Two sets of plastic test items were inoculated by rinsing through with 10 ml of 1×10$^4$ cfu/ml *Bacillus cereus*. One set of items was not treated and used as a control. The other set of items was placed in a heatable and sealable container along with a single sachet containing the formulation which had been injected with 10 ml of water (using a syringe and needle). A standard hydrogen peroxide colourimetric test strip (eg Merck KGaA, Darmstadt, Germany) was also placed within the container. The container was then sealed and heated to 50° C. for about 30 minutes.

Discussion

At completion of the heating, the container was opened and the test strip was observed to have changed colour indicating that hydrogen peroxide had been generated and escaped from the sachet. The items were then thoroughly rinsed with 10 ml of peptone solution to remove all surviving bacterial populations. No bacterial growth was generated from the rinse following plating and culture on sterile agar plates indicating that complete kill had been achieved (ie a reduction of 1.77 logs was achieved from the 60 cfu/ml determined to be present on the items at the start of the disinfection process). The results indicate that the present invention may be adapted for uses in disinfecting items (eg baby bottles and food containers). In particular, it may be desirable to provide the formulation as a tablet or pellet. Such a tablet or pellet may be formed by compressing the formulation (optionally in the presence of a suitable binding agent) with a standard tablet press. Additionally or alternatively, the tablet or pellet might comprise a water-soluble external film or coating. The formulation may also comprise, for example, a disintegrant (eg cross-linked polyvinylpyrrolidone and other disintegrant excipients well known to those skilled in the art) to facilitate the tablet breaking apart upon exposure to water or water vapour.

Example 4

Use of Device for Removal of Ethylene in Cool Room

Device

Ethylene present in cool rooms where horticultural products are stored can cause problems such as over-ripening of fruit and advanced ageing and yellowing of fruits and vegetables. In this example, the effectiveness of a sachet device according to the invention for the removal of ethylene in such cool rooms was tested. The formulation was prepared as described in Example 1 and placed (in amounts of about 120 g) into 13 cm×20 cm sachets composed of a membrane of Tyvek®). The sealed sachets were then packaged in a moisture- and vapour-impermeable HDPE bag until use.

Cool Room and Test Method

For the purposes of the test, the cool room was provided with 20 ppm of ethylene. This is considerably higher than the levels of about 0.1 to 3 ppm ethylene that are typically reported as being present in cool rooms with stored horticultural products. Air sampling and ethylene analysis was conducted using a standard GC with flame ionisation detector (GC-FID; Shimadzu 15C, Shimadzu Corporation, Kyoto, Japan). The cool room used in the test was a typical mobile cool room of 8 $m^3$ in volume. The cool room was set to an internal temperature of 3° C. and the refrigeration unit maintained the temperature to within 1.5° C. of the set point when under stable running condition. The cool room was provided with two 15 L water containers and towels wicking water from each container onto a low shelf within the cool room (thereby providing a source of water vapour). A fan was placed within the cool room to ensure mixing of the air for sampling. The sachet device was affixed in a vertical position to a wall of the cool room. For each test, the experimental apparatus was set up in the cool room and then the temperature was allowed to stabilise. Once the temperature had stabilised, the production of hydrogen peroxide vapour was activated by injecting 25 ml of water into the sachet device. The internal temperature of the cool room was then given a further ten minutes to stabilise. The test was then started by the injection of 160 ml of 99.9% ethylene gas into the room (2×80 mls, flushed with a further 100 mls of air). After five minutes, the first air sample was taken. Sampling was performed for up to 24 hours.

Results

Figure 2:
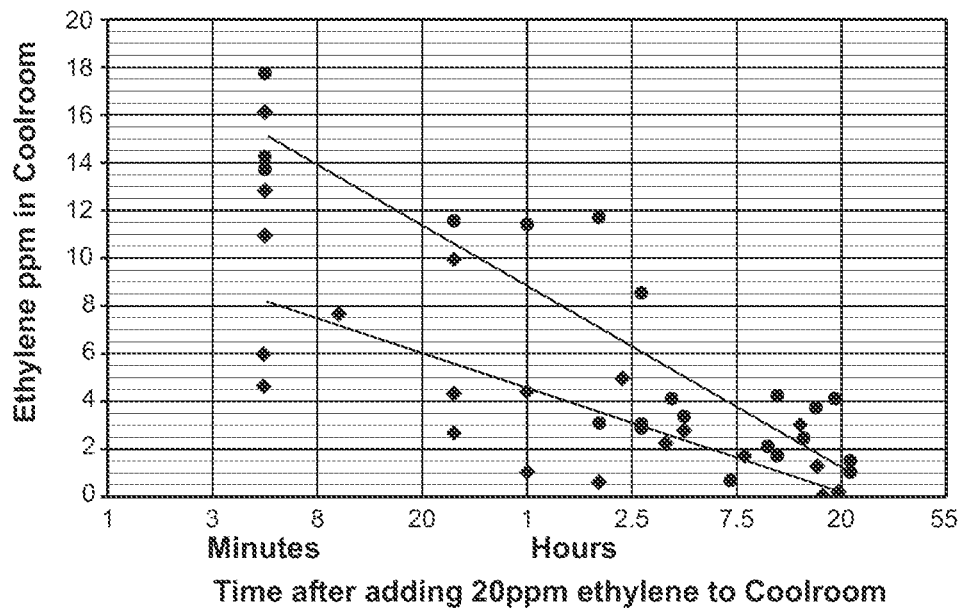
FIG. 2 provides the results of tests conducted to investigate the effectiveness of a sachet device of the invention to reduce the ethylene concentration in a cool room with stored horticultural products. Logarithmic decay was observed in the ethylene levels over time (control: $y=-2.5464*\ln(x)+8.8176$, $R^2=0.79476$; and sachet device: $y=-1.4500*\ln(x)+4.5441$, $R^2=0.6011$)

The results are shown in FIG. 2. Although the precise amount of ethylene was added to give a concentration of 20 ppm in a volume of 8 $m^3$, a significant amount of ethylene was lost in the first 5 minutes. The initial decline was especially large in the presence of a sachet device; indicating a rapid breakdown of ethylene by the newly activated device sachet. The decline in ethylene concentration for both the device and control tests is initially rapid and then declines over time in a classic logarithmic decay. As can be seen from FIG. 2, after 5 minutes the ethylene levels had been virtually halved from the control level of 15.1 ppm to 8.1 ppm in the presence of a sachet device. After 1 hour, the ethylene levels were again virtually halved to 4.5 ppm in the presence of a sachet device.

Discussion

The results clearly show that devices according to the present invention can be very effective in reducing ethylene levels in commercial cool room storage conditions, even when the ethylene levels are as high as 20 ppm.

Example 5

Use of Device for Reducing Bacteria in Cool Room

Device

In this example, the effectiveness of the sachet device according to the invention for bacterial reduction in a cool room was tested. The formulation was prepared as described in Example 1 and placed (in amounts of about 120 g) into 13 cm×20 cm sachets composed of a membrane of Tyvek®. The sealed sachets were then packaged in a moisture- and vapour-impermeable HDPE bag until use.

Cool Room and Test Method

A 10 $m^3$ cool room in a commercial food retail business was used in the tests. The cool room used a forced draft chiller (FDC) unit fan. A single sachet device was affixed in a vertical position to a wall of the cool room. Swabs were taken from a quarter portion of the fan cover at 21 day intervals and analysed using standard plate count (SPC) methodology.

Results

Figure 3:
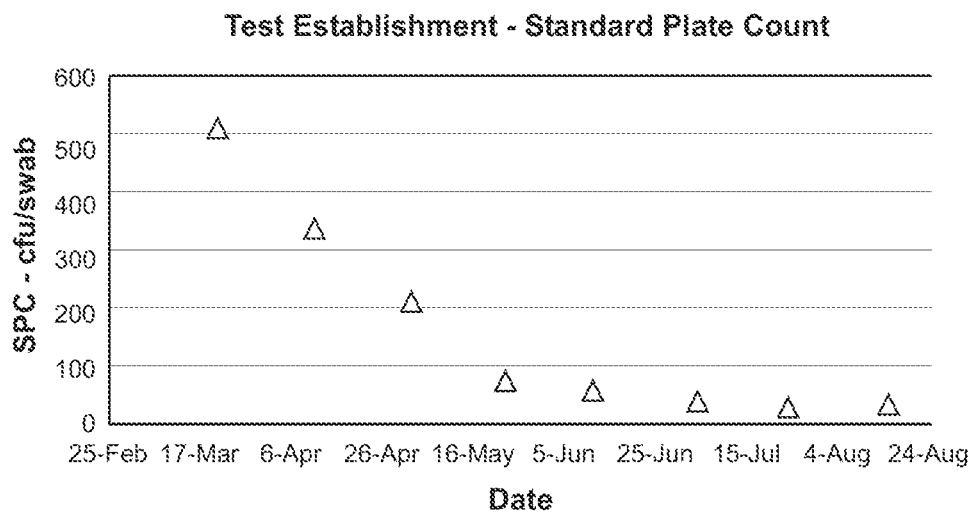
FIG. 3 provides the results of a test conducted to investigate the bacterial reduction capacity of a sachet device of the invention in a commercial cool room. The test was conducted over about a 6 month period from 25 Feb. to 24 Aug. 2014. The level of bacteria was measured by taking swabs from the cool room at 20 day intervals and analysing the swabs using a standard plate count (SPC) methodology.

The results are shown in FIG. 3. The initial SPC taken immediately before the sachet device was introduced into the cool room (on 25 February) was 500 cfu/swab. Within 3 weeks, this level had been reduced to about 200 cfu/swab. 9 weeks later, the level had dropped to <100 cfu/swab; a level that was then maintained for the remainder of the trial.

Discussion

The results clearly show that devices according to the present invention can be very effective in reducing bacteria in cool rooms. In this test, one device was able to reduce the bacterial level to <100 cfu/swab, and then maintain it at that level or lower for at least 12 weeks.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the invention is not restricted in its use to the particular application described. Neither is the present invention restricted in its preferred embodiment with regard to the particular elements and/or features described or depicted herein. It will be appreciated that the invention is not limited to the embodiment or embodiments disclosed, but is capable of numerous rearrangements, modifications and substitutions without departing from the scope of the invention as set forth and defined by the following claims.

The invention claimed is:

1. A system comprising:
   a vapour-permeable container in the form of a sealed sachet which is impermeable to water liquid and/or droplets, the vapour-permeable container having walls defining a single internal housing space;
   an admixture disposed within the single internal housing space of the vapour-permeable container consisting of a moisture-removing material, a solid substrate having a specific surface area (SSA) of >100 $m^2$ $g^{-1}$, and a hydrogen peroxide-generating material;
   wherein the hydrogen peroxide-generating material is selected from the group consisting of sodium percarbonate, hydrated sodium perborate, organic or inorganic peroxy salts, and combinations thereof; and
   wherein the admixture of the said moisture-removing material, solid substrate and hydrogen peroxide-generating material is provided such that water vapour entering the single internal housing space causes the hydrogen peroxide-generating material to generate an antimicrobial vapour of hydrogen peroxide which permeates from the vapour-permeable container.

2. The system of claim 1, wherein the moisture-removing material is selected from the group consisting of calcium chloride and calcium sulphate.

3. The system of claim 1, wherein the hydrogen peroxide-generating material is sodium percarbonate.

4. The system of claim 1, wherein the solid substrate is precipitated silica.

5. The system of claim 4, wherein the moisture-removing material, the hydrogen peroxide-generating material and the solid substrate are provided as the admixture comprising, by percentage weight of the admixture, 20-40 wt % of the moisture-removing material, 10-20 wt % of the hydrogen peroxide-generating material and 45-65 wt % of the solid substrate.

* * * * *